(12) United States Patent　　　(10) Patent No.:　　US 12,632,243 B2

Haldar　　　　　　　　　　　　　(45) Date of Patent:　　**\*May 19, 2026**

(54) REMOTE SYSTEM MONITORING AND FIRMWARE-OVER-THE-AIR UPGRADE OF ELECTROSURGICAL UNIT

(71) Applicant: Medtronic, Inc., Minneapolis, MN (US)

(72) Inventor: Snehashis Haldar, Coimbatore (IN)

(73) Assignee: Medtronic, Inc., Minneapolis, MN (US)

( * ) Notice: Subject to any disclaimer, the term of this patent is extended or adjusted under 35 U.S.C. 154(b) by 45 days.

This patent is subject to a terminal disclaimer.

(21) Appl. No.: 18/643,811

(22) Filed: Apr. 23, 2024

(65) Prior Publication Data

US 2024/0303072 A1　　　Sep. 12, 2024

Related U.S. Application Data

(63) Continuation of application No. 17/679,648, filed on Feb. 24, 2022, now Pat. No. 11,995,431.

(60) Provisional application No. 63/200,255, filed on Feb. 24, 2021.

(51) Int. Cl.
　　*G06F 8/65*　　　　　(2018.01)
　　*G16H 40/40*　　　　(2018.01)

(52) U.S. Cl.
　　CPC ............... *G06F 8/65* (2013.01); *G16H 40/40* (2018.01)

(58) Field of Classification Search
　　CPC .. G06F 8/65; G06F 2201/805; G06F 11/1433; G06F 11/1479; G16H 40/40; G16H 40/67
　　See application file for complete search history.

(56) References Cited

U.S. PATENT DOCUMENTS

| | | | | |
|---|---|---|---|---|
| 8,600,685 | B2 * | 12/2013 | Kalgren | ................. G01D 18/00 |
| | | | | 702/182 |
| 11,934,755 | B2 * | 3/2024 | Sundararajan | .......... G06F 30/17 |
| 2015/0193325 | A1 * | 7/2015 | Harsan-Farr | .......... G06F 11/008 |
| | | | | 702/186 |
| 2015/0281015 | A1 * | 10/2015 | Griffith | ............... H04L 43/0817 |
| | | | | 709/224 |
| 2017/0286572 | A1 * | 10/2017 | Hershey | .................... B64F 5/60 |
| 2018/0054376 | A1 * | 2/2018 | Hershey | ................ H04L 43/067 |
| 2019/0059982 | A1 | 2/2019 | Smith et al. | |
| 2019/0087544 | A1 | 3/2019 | Peterson | |
| 2019/0163147 | A1 * | 5/2019 | D'Amato | ................ G06F 17/16 |
| 2019/0187776 | A1 * | 6/2019 | Mukherjee | ............ G06F 1/3203 |
| 2020/0185107 | A1 * | 6/2020 | Cox | ....................... G16H 50/50 |
| 2020/0211699 | A1 | 7/2020 | Nuthi et al. | |

(Continued)

FOREIGN PATENT DOCUMENTS

| | | | |
|---|---|---|---|
| CN | 111078243 A | 4/2020 | |
| WO | WO 2010/141922 A1 | 12/2010 | |
| WO | WO-2015023201 A2 * | 2/2015 | ............ G06F 11/008 |

OTHER PUBLICATIONS

Application and File History of U.S. Appl. No. 17/679,648, filed Feb. 24, 2022. Inventors Haldar.

*Primary Examiner* — Daxin Wu

(74) *Attorney, Agent, or Firm* — Husch Blackwell LLP

(57) ABSTRACT

Systems and methods for monitoring an electrosurgical unit (ESU), analyzing ESU system data, predicting future ESU maintenance, and updating the ESU using firmware over-the-air (FOTA).

14 Claims, 5 Drawing Sheets

(56)        References Cited

U.S. PATENT DOCUMENTS

2021/0133670 A1 *   5/2021   Cella ...................... G06N 3/044
2021/0350294 A1     11/2021   Johnson et al.

* cited by examiner

100

200

300

400

500

Data from ESU

CLOUD
502

Data from ESU

Virtual Model of ESU
504

Predictive Mechanism
of Fault Detection /
Fault Identification
506

FAULT Fixing /
Enhancement of
Function in Firmware
508

Firmware update

CLOUD
502

REMOTE SYSTEM MONITORING AND FIRMWARE-OVER-THE-AIR UPGRADE OF ELECTROSURGICAL UNIT

CROSS-REFERENCE TO RELATED APPLICATIONS

This application is a continuation of U.S. application Ser. No. 17/679,648 filed Feb. 24, 2022, which claims the benefit of U.S. Provisional Application No. 63/200,255, filed Feb. 24, 2021, the disclosures of which are hereby incorporated by reference in their entireties.

FIELD

The present technology is generally related to medical devices, and more particularly, to electrosurgical unit (ESU) devices, systems, and methods.

BACKGROUND

Medical devices, such as electrical surgical units, are used by medical professionals in surgical procedures. Traditionally, ESU devices operate in a surgical environment without access to outside systems. Accordingly, for any service or repair of an ESU, the device must be serviced by an on-site repairman or returned to a service center.

Moreover, during servicing, in order to load new or updated firmware or software, a separate computing device is physically connected to an ESU using a serial cable or Ethernet cable. Accordingly, updating or servicing ESUs is costly and time-consuming.

Therefore, there is a need for systems and methods for more efficiently managing ESU devices.

SUMMARY

The techniques of this disclosure generally relate to systems and methods for remotely monitoring, maintaining, and upgrading an ESU.

In one aspect, the present disclosure provides a system for dynamically and remotely monitoring, maintaining, and upgrading an electrosurgical unit (ESU). The system comprises a remote system including computing hardware of at least one processor and memory operably coupled to the at least one processor. The remote system is configured to: receive system data over a network from the ESU, the ESU including ESU hardware of a plurality of hardware components and ESU firmware configured to operate with the plurality of hardware components, wherein the system data is received at a periodic rate and in response to an event on the ESU, and is received wirelessly at the network from the ESU; generate a digital twin data model of the ESU, the digital twin data model being remote from the ESU; predict a fault on the ESU based on the digital twin data model; generate a firmware update based on the predicted fault, the firmware update being direct to at least one of the plurality of hardware components; and transmit the firmware update over the network to the ESU, wherein the firmware update is transmitted wirelessly from the network to the ESU, and once installed, updates operation of the at least one of the plurality of hardware components.

In another aspect, the present disclosure provides a method for dynamically and remotely monitoring, maintaining, and upgrading an electrosurgical unit (ESU). The method comprises: receiving system data over a network from the electrosurgical unit (ESU), the ESU including ESU hardware of a plurality of hardware components and ESU firmware configured to operate with the plurality of hardware components, wherein the system data is received at a periodic rate and in response to an event on the ESU, and is received wirelessly at the network from the ESU; generating a digital twin data model of the ESU, the digital twin data model being remote from the ESU; predicting a fault on the ESU based on the digital twin data model; generating a firmware update based on the predicted fault, the firmware update being direct to at least one of the plurality of hardware components; and transmitting the firmware update over the network to the ESU, wherein the firmware update is transmitted wirelessly from the network to the ESU, and once installed, updates operation of the at least one of the plurality of hardware components.

In another aspect, the present disclosure provides a non-volatile computer readable storage medium comprising instructions that, when executed by a processor, cause the processor to: receive system data over a network from an electrosurgical unit (ESU), the ESU including ESU hardware of a plurality of hardware components and ESU firmware configured to operate with the plurality of hardware components, wherein the system data is received at a periodic rate and in response to an event on the ESU, and is received wirelessly at the network from the ESU; generate a digital twin data model of the ESU, the digital twin data model being remote from the ESU; predict a fault on the ESU based on the digital twin data model; generate a firmware update based on the predicted fault, the firmware update being direct to at least one of the plurality of hardware components; and transmit the firmware update over the network to the ESU, wherein the firmware update is transmitted wirelessly from the network to the ESU, and once installed, updates operation of the at least one of the plurality of hardware components.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
FIG. 1 is a block diagram of a system including an ESU, according to an embodiment.
Figure 1:
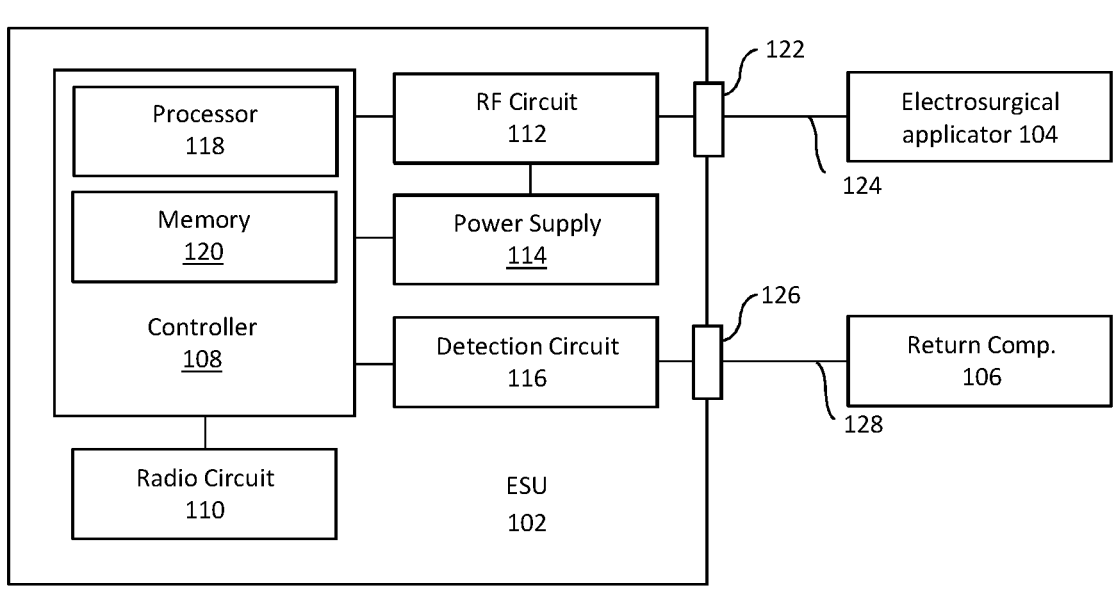

Embodiments relate generally to medical devices, systems, and methods for use in surgical procedures. More specifically, this disclosure relates to electrosurgical devices, systems and methods that provide for cutting, coagulation, hemostasis, or sealing of bodily tissues including bone with an electrosurgical device. Embodiments further relate to operations involving the management of the device itself, such as systems and methods for monitoring an electrosurgical unit, analyzing ESU system data, predicting future ESU maintenance, and updating the ESU using firmware over-the-air (FOTA).

Electrosurgery includes such techniques as cutting, coagulation, hemostasis, and/or sealing of tissues with the aid of electrodes energized with a suitable power source. Typical electrosurgical devices apply an electrical potential difference or signal between an active electrode and a return electrode on a patient's grounded body in a monopolar arrangement or between an active electrode and a return electrode on the device in bipolar arrangement to deliver electrical energy to the area where tissue is to be affected. The electrosurgical devices are typically held by the surgeon and connected to the power source, such as an electrosurgical unit having a power generator, via cabling.

Electrosurgical devices pass electrical energy through tissue between the electrodes to provide coagulation to control bleeding and hemostasis to seal tissue. Electrosurgical devices can also cut tissue through the use of plasma formed on the electrode. Tissue that contacts the plasma experiences a rapid vaporization of cellular fluid to produce a cutting effect. Typically, cutting and coagulation are often performed with electrodes in the monopolar arrangement while hemostasis is performed with electrodes in the bipolar arrangement.

Electrical signals can be applied to the electrodes either as a train of high frequency pulses or as a continuous signal typically in the radiofrequency (RF) range to perform the different techniques. The signals can include a variable set of parameters, such as power or voltage level, waveform parameters such as frequency, pulse duration, duty cycle, and other signal parameters that may be particularly apt or preferred for a given technique. For example, a surgeon could cut tissue using a first RF signal having a set of parameters to form plasma and control bleeding using a second RF signal having another set of parameters more preferred for coagulation.

As discussed herein, ESU firmware generally refers to "embedded software", "firmware", or "micro-code" involved with very basic low-level operations of ESU device hardware. Firmware is typically held in non-volatile memory as fixed data as part of a particular hardware component. Further, the term "firmware" is relative in that an ESU can contain firmware at more than one level; such as CPUs, flash chips, communication controllers, LCD modules, etc.

ESU software generally refers to a higher-level "application" software configured to ensure that appropriate energy is delivered to the patient or interact with the user. ESU software can include the aforementioned parameters for controlling electrical signals, and/or operations with the aforementioned parameters.

With respect to the management of ESU devices, embodiments described herein can be utilized for ESU firmware or software, or various combinations of both firmware and software. When the terms "firmware" or "firmware over-the-air" are used herein, one of ordinary skill in the art will appreciate that "software" can likewise be interchanged with "firmware," such that software can handled in a similar manner to firmware.

Referring to FIG. 1, a block diagram of a system 100 including an ESU 102 is depicted, according to an embodiment. System 100 further comprises an electrosurgical applicator 104 electrically coupled to ESU 102 and a return component 106 electrically coupled to ESU 102.

In general, ESU 102 provides RF energy to an active electrode on electrosurgical applicator 104 to be applied to tissue of a patient and receives a return signal via return component 106 in contact with the patient. ESU 102 is able to detect electrical characteristics (impedance, components of impedance such as resistance or reactance, or their changes) of the signal passing through the patient between electrosurgical applicator 104 and return component 106 to provide information regarding the viability of the tissue adjacent to return component 106.

ESU 102 generally comprises a controller 108, a radio circuit 110, an RF circuit 112, a power supply 114, and a detection circuit 116. ESU 102 can further include one or more output connections 122 and one or more return receptacles 126.

As depicted, ESU 102 includes one or more active electrode output connections 122 that is configured to be electrically coupled to electrosurgical applicator 104, such as an electrosurgical device configured in a monopolar mode, and one or more return electrode receptacles 126, one of which is configured to be coupled to return component 106. Example ESU 102 can include a controller 108, an RF output circuit 112, and a high voltage power supply 114. The power supply 114 provides high voltage power to RF output circuit 112, which converts high voltage power, for example from a direct current, into RF energy and delivers the RF energy to active electrode output connection 122. RF output circuit 112 is configured to generate a plurality of waveforms having various duty cycles, peak voltages, crest factors, and other suitable parameters.

In embodiments, ESU 102 can include one or more outputs 122 including a monopolar mode output, a bipolar output, or a combination monopolar and bipolar output, which be electrically coupled to an active electrode 124 to electrosurgical applicator 104. In embodiments, ESU 102 can also include one or more return receptacles 126 that can be electrically coupled to return component 106 via a return electrode 128.

Controller 108 can include a processor 118 operably connected to a memory device 120. Examples of a memory device 120 can include a non-volatile memory device such as a read only memory (ROM), electronically programmable read only memory (EPROM), flash memory, non-volatile random access memory (NVRAM) or other memory device, and a volatile memory device such as random access memory (RAM) or other memory device. Memory device 120 can include various combinations of one or both of non-volatile memory devices and volatile memory devices. Processor 118 includes an output port that is operably connected to RF output circuit 112, power supply 114, or both, that allows processor 118 to control the output of ESU 102 according to a selected scheme. In some examples, processor 118 can be substituted with a logic processor or other control circuit. As will be described, controller 108 is further connected to radio circuit 110.

Any combination of hardware and programming may be used to implement the functionalities of ESU 102. Such combinations of hardware and programming may be implemented in a number of different ways. For example, the programming for ESU 102 can be processor executable instructions stored on at least one non-transitory machine-readable storage medium, such as memory device 120 and the hardware may include at least one processing resource, such as processor 118, to execute those instructions. In some examples, the hardware may also include other electronic circuitry to at least partially implement at least one feature of ESU 102. In some examples, the at least one machine-readable storage medium, such as a memory device 120, can store instructions that, when executed by processor 118, at least partially implement some or all features of ESU 102. In such examples, ESU 102 can include the at least one machine-readable storage medium storing the instructions and the at least one processing resource to execute a method. In other examples, the functionalities of ESU 102 and corresponding methods can be at least partially implemented in the form of electronic circuitry. Accordingly, ESU 102 and its various components can be implemented by hardware, firmware, and/or software.

ESU 102 also includes detection circuit 116 electrically coupled to return receptacle 126 and operably coupled to controller 108. The features and functions described below as included in the detection circuits such as detection circuit 116, in this disclosure may be, in some examples, included in or performed with controller 108, vice versa, or some other combination. Furthermore, features and functionality of the detection circuits, such as detection circuit 116, can be implemented from one or more of conductors, circuit elements, hardware, firmware, and/or software. Detection circuit 116 and controller 108 operate together to determine the impedance over time in the tissue forming an electrical path between active electrode 124 and return component 106 while treating tissue during surgery.

ESU 102 further comprises radio circuit 110, which can be operably coupled to controller 108. Radio circuit 110 comprises one or more electronic elements configured to transmit and receive data related to system 100. For example, radio circuit 110 can be configured for radio frequency (RF) communications, WIFI communications, BLUETOOTH low energy (BLE) communications, or near-field communications (NFC). Other suitable communication circuitries can likewise be utilized. In embodiments, any of LoRaWAN, MQTT, CoAP; HTTPS & SSL can be utilized for secure data exchange. In embodiments, FTP/FTPS can be utilized for file transfer. In further embodiments, proprietary protocols can be utilized. Accordingly, radio circuit 110 is configured to communicate with one or more computing devices remote from system 100.

In embodiments, system 100 and ESU 102 can be monitored by algorithms of controller 108. In particular, controller 108 can determine, record, or otherwise define the functionality, operating parameters, errors, and/or other characteristics of system 100, including data or details of individual components of system 100. In general, such data can be referred to as "system data." In embodiments, controller 108 is further configured to provide system data to radio circuit 110. In turn, radio circuit 110 can transmit system data to the one or more computing devices remote from system 100.

Radio circuit 110 is further configured to receive firmware and software updates from one or more computing devices remote from system 100 and provide such updates to controller 108. In turn, controller 108 is further configured to update ESU 102 components according to the received updates.

Figure 2:
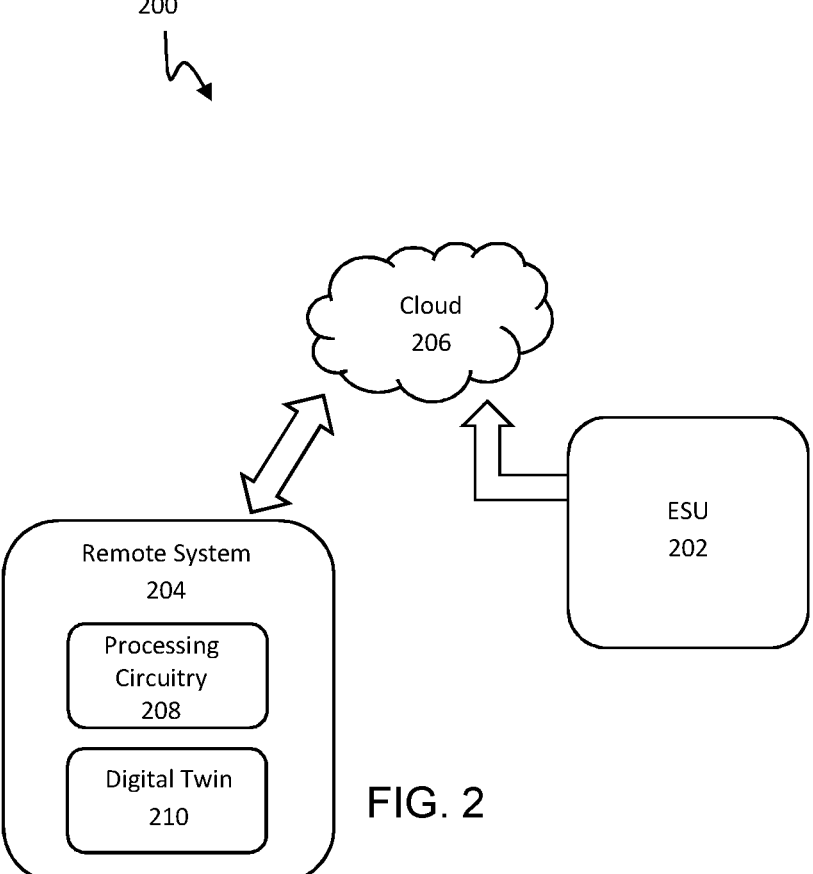
FIG. 2 is a block diagram of a system including an ESU, according to an embodiment.

Referring to FIG. 2, a block diagram of a system 200 is depicted, according to an embodiment. System 200 generally comprises an ESU 202, a centralized remote system 204, and a cloud-based network 206 operably coupling ESU 202 and centralized remote system 204.

ESU 202 is substantially similar to ESU 102 as depicted and described with respect to FIG. 1, but is renumbered here for case of explanation. Accordingly, ESU 202 comprises (among other components), a radio circuit in communication with cloud-based network 206.

Centralized remote system 204 comprises processing circuitry 208 and storage for a digital twin 210. Processing circuitry 208 generally comprises at least one processor and memory operably coupled to the processor. The at least one processor is programmable device that accepts digital data as input, is configured to process the input according to instructions or algorithms, and provides results as outputs. In an embodiment, the processor can be a central processing unit (CPU) configured to carry out the instructions of a computer program. The at least one processor is therefore configured to perform at least basic arithmetical, logical, and input/output operations.

The memory operably coupled to the at least one processor can comprise volatile or non-volatile memory as required by the coupled at least one processor to not only provide space to execute the instructions or algorithms, but to provide the space to store the instructions themselves. In embodiments, volatile memory can include random access memory (RAM), dynamic random access memory (DRAM), or static random access memory (SRAM), for example. In embodiments, non-volatile memory can include read-only memory, flash memory, ferroelectric RAM, hard disk, floppy disk, magnetic tape, or optical disc storage, for example. The foregoing lists in no way limit the type of memory that can be used, as these embodiments are given only by way of example and are not intended to limit the scope of the disclosure.

As will be described, processing circuitry 208 can utilize data from one or more physical assets, such as ESU 202, to analyze the efficiency, condition, and real-time status of the asset. Processing circuitry 208 is further configured to receive event-based and/or periodic reports related to ESU 202.

Processing circuitry 208 is further configured to generate firmware or software updates for ESU 202 or components of ESU based on the analyzing and communicate such updates back to ESU 202 over cloud-based network 206. Accordingly, centralized remote system 204 is likewise communicatively coupled with cloud-based network 206.

In an embodiment, digital twin 210 comprises a mapping of ESU 202 to a digital platform. In embodiments, digital twin 210 comprises a database, data store, model, or other suitable mapping of ESU 202 that can be utilized by processing circuitry 208 to analyze one or more ESUs 202. In an embodiment, digital twin 210 can be stored or managed in a grid computing system.

Data included in digital twin 210 can include operational data such as sensed power, current, voltage, temperature, and waveform parameters such as frequency, duty cycle etc. In embodiments, data included in digital twin 210 can further include more hardware-specific data such as ESU 202 processor capability, ESU 202 memory capability, ESU radio circuit status, ESU RF circuit status, ESU power supply status, ESU detection circuit status, etc.

Cloud-based network 206 can be a singular "cloud" or network, or spread among many clouds or networks. ESU 202 end-user knowledge of the physical location and configuration of components of cloud-based network 206 is not required. Cloud-based network 206 can comprise one or more computing devices to transmit, forward, or otherwise package data between ESU 202 and remote system 204.

Figure 3:
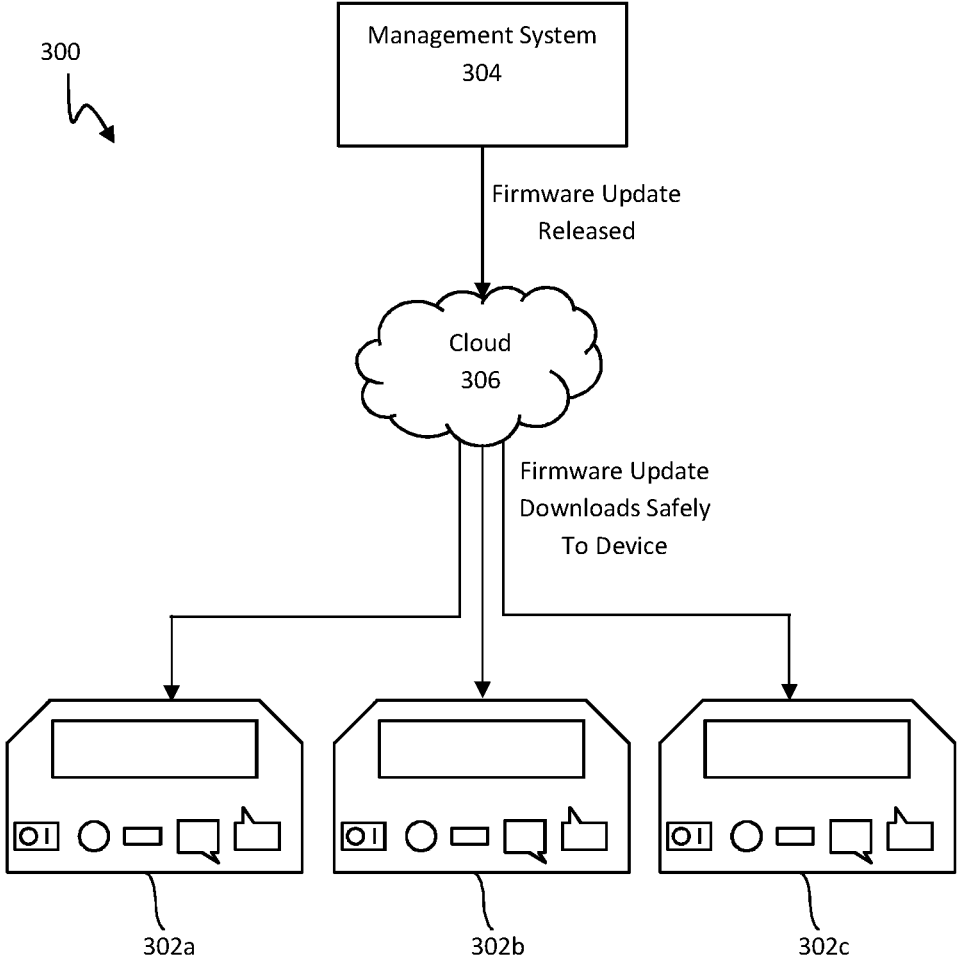
FIG. 3 is a block diagram of a system for updating an ESU, according to an embodiment.

Referring to FIG. 3, a block diagram of a system 300 for updating an ESU using FOTA is depicted, according to an embodiment. System 300 generally comprises management system 304, one or more ESUs 302a, 302b, 302c, and a network cloud 306 operably coupling one or more ESUs 302a, 302b, 302c and management system 304.

Firmware over-the-air (FOTA) updates are aimed at fixing software or firmware issues, improving functionality of an ESU system, and replacing old firmware with newer versions. In embodiments, the ESU being updated can be located at any location having access to a network; for example, at a distributed clinic location, on a production line, or at a retail/seller location.

ESUs 302a, 302b, 302c can be substantially similar to ESU 102 and ESU 202 as depicted and described with respect to FIGS. 1-2, but are renumbered here for case of explanation.

Management system 304 can be substantially similar to remote system 204 as depicted and described with respect to FIG. 2, but is renumbered here for ease of explanation.

Network cloud 306 can be substantially similar to cloud-based network 206 as depicted and described with respect to FIG. 2, but is renumbered here for case of explanation.

In operation, management system 304 can generate a firmware update for one or more ESUs 302a, 302b, 302c. For example (although not depicted in FIG. 3), management system 304 can receive system data from one or more ESUs 302a, 302b, 302c and model the system data as a digital twin. In embodiments, a separate digital twin can be stored and/or modeled for each ESU 302a, 302b, 302c. In other embodiments, an aggregated digital twin can incorporate data from multiple ESUs. From the digital twin, a firmware update can be generated. The firmware update can be specific to one of the ESUs 302a, 302b, 302c, or applicable to all ESUs 302a, 302b, 302c.

Management system 304 transmits the update to network cloud 306, which relays the update to one or more ESUs 302a, 302b, 302c. In an embodiment, only one ESU 302a, 302b, 302c downloads the update (if, for example, the update is specific to that particular ESU). In another embodiment, two or more of the ESUs 302a, 302b, 302c download the update (if, for example, the update is applicable to multiple ESUs).

In embodiments, a firmware update can be batched or temporarily stored at management system 304 or network cloud 306. For example, if a particular ESU is operational in a surgical procedure, the radio circuit in that ESU can be disabled for downloading. Once the particular ESU is not in use or has a designated download time, the firmware update can be downloaded.

Once downloaded, a firmware update can be temporarily stored but not installed in an ESU. In another embodiment, once downloaded, the firmware update can be automatically installed in the ESU.

In an embodiment, firmware updating is conditional and can be based on or accepted through user input via the ESU touch screen, or by using predetermined updating rules.

Embodiments implement intelligent download and/or install timings. In an embodiment, for a firmware update having an enhancement, a maintenance cycle (e.g. quarterly once or yearly twice or yearly once) can be created and communicated to a customer beforehand (for example, in a product manual, etc.)

For a critical bug fix, firmware can be updated in ad hoc method. Normally, during power cycle of an ESU, an option can be presented on the LCD screen indicating firmware update availability and to seek permission from the user to update. Based on permission provided by a user, the update process can then be started.

In an embodiment, because a firmware update is done during a power cycle, there is no possibility of patient interaction at that time. For other security during communication with the remote server, appropriate cyber security protocols are applied.

Further, as part of the update process, a backup copy of the existing firmware is be created and in case of an install error, a fallback operation to restore the backup copy is executed.

Figure 4:
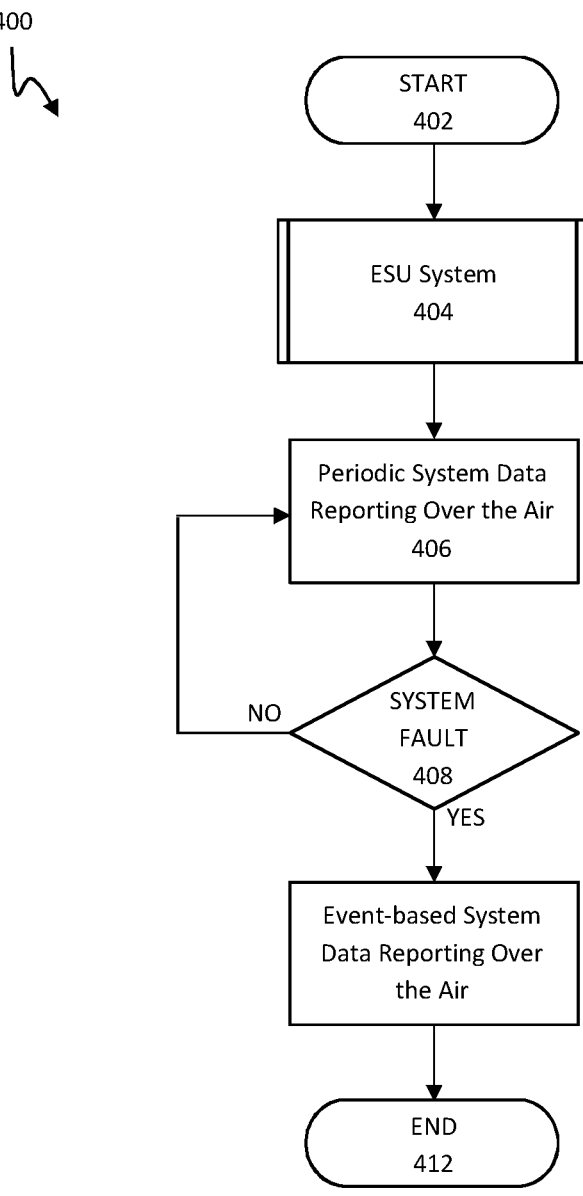
FIG. 4 is a flowchart of a method for ESU system monitoring and reporting, according to an embodiment.
Figure 5:
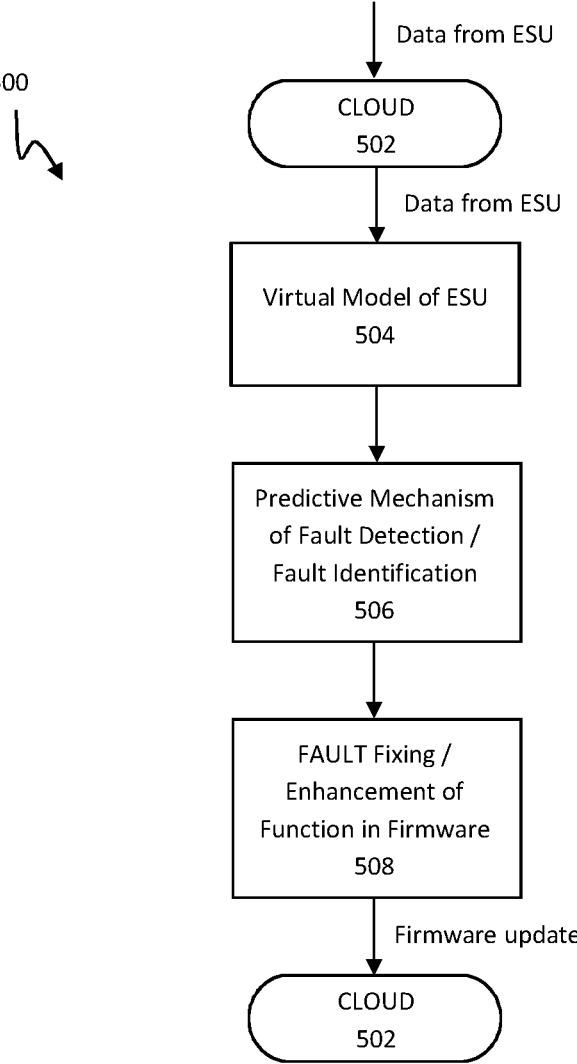
FIG. 5 is a flowchart of a method for ESU fault prediction and fault handling, according to an embodiment.

Referring generally to FIGS. 4-5, methods for operating a system having an ESU include periodic and/or event-based monitoring and reporting paired with over-the-air updating. In embodiments, an ESU monitors and reports the real time system data which is used by a remote digital twinning system to analyze and predict the need for maintenance and/or part replacements of an ESU.

Referring specifically to FIG. 4, a flowchart of a method 400 for ESU system monitoring and reporting is depicted, according to an embodiment. Method 400 generally comprises starting at 402 on an ESU or ESU system. In embodiments, ESU system 404 can be automatically started upon power-up for reporting, can be triggered to start reporting (e.g. according to a particular event or timing), or can be manually started for reporting by a user.

In another embodiment, ESU system 404 can be remotely started for reporting, such as by a remote management system. In certain embodiments, the remote management system can periodically or ad-hoc communicate with the ESU to initiate a given reporting. In other embodiments, once started, the ESU automatically communicates with the remote management system according to instructions in the ESU.

At 406, system data can be periodically reported by an ESU to a remote management system over the air using a network. The period can be predefined according to the state of the ESU. For example, during standby operation (e.g. not actively in a surgical procedure), system data can be reported at a less frequent rate than during active use (e.g. surgery). During active use, for example, the periodic reporting can be every 20-30 ms. In other embodiments, the period can be defined by a user.

At 408, if a system fault is detected by the ESU, a non-periodic reporting is made at 410. For example, if the ESU detects a spike in some component, an event-based reporting is transmitted to the remote management system. In embodiments, a real-time operating system provided in the ESU can readily handle combined periodic and event-based reporting. If no fault is detected at 408, method 400 returns to periodic reporting at 406.

At 412, method 400 ends. Method 400 thus assumes an error from ESU that prohibits ESU from continuing operation. In another embodiment, at depicted in dashed line from 410, method 400 can return to periodic system data reporting at 406; for example, if the system fault detected at 408 allows ESU to continue operation.

Referring to FIG. 5, a flowchart of a method 500 for ESU fault prediction and fault handling is depicted, according to an embodiment. Method 500 generally comprises receiving data from an ESU at cloud 502. From 502, the ESU data can be input into a virtual model at 504, such as a digital twin on a remote management system. Using digital twinning, the remote ESU model can be maintained by device manufacturers or otherwise kept secret.

At 506, management system can make one or more predictions based on the digital twin model. For example, a prediction can be a future fault determination or future issue determination. In an embodiment, the prediction can be a determination of the remaining useful life of a particular ESU component. In an embodiment, machine learning, artificial intelligence, or other predictive algorithms can be utilized to make the prediction.

In an embodiment, regarding predicting relay stickiness detection, based on a frequency of relay stickiness and a degree of relay stickiness (easily recoverable, not easily recoverable, etc.) data, a predictive maintenance model can be created to detect the Remaining Useful Life (RUL) of the relay.

At 508, after an issue is detected or predicted, a firmware update can be generated to fix or address the issue. For example, if a particular component is predicted to fail, firmware can be updated to operate the ESU differently such that the failing component is used less or is not used at all. The firmware update therefore protects the at-issue component. In another embodiment, an enhancement can be implemented via the firmware update such that the prediction at 506 is not specific to a particular fault or issue, but rather a general enhancement request.

In an embodiment, once the RUL for a particular component is made, an analysis is conducted to determine if the RUL can be extended via software or firmware. If RUL can be extended, a firmware solution is created. The solution is tested on the digital twin prior to uploading to the ESU.

In certain embodiments, method 500 therefore can create specific firmware or software unique to each ESU.

From 508, the firmware update is transferred to cloud 502 and subsequently to the particular ESU at issue. In certain embodiments, a message can be presented to the user that the ESU or a particular component of the ESU will fail after a certain time or number of cycles, etc. (whatever is predicted). User messages can be utilized in combination with the firmware update, or on their own as the deliverable back to the ESU.

Accordingly, embodiments described herein are more cost efficient than traditional solutions. In particular, device manufacturers or other appropriate users can seamlessly manage firmware updates across a fleet of ESUs from one unified interface. The costs significantly decrease over the entire lifecycle of the ESU.

In another feature and advantage, firmware over-the-air programming does not require a separate computing device to be physically connected to the ESU. For example, by utilizing a radio module of the ESU and over-the-air data transmission (such as WIFI or BLE) and programming through the ESU bootloader, the product firmware can be updated.

In another feature and advantage, embodiments described herein offer continuous improvement compared to traditional solutions. In particular, software issues can be fixed or updated, and product behavior can be enhanced after the device is with the consumer. This can potentially eliminate costly recalls and in-person maintenance.

In another feature and advantage, embodiments described herein offer improved scalability compared to traditional solutions. FOTA updates allow device manufacturers or appropriate users to add new features to infrastructure after a device release without physical access to the device in order to upgrade firmware.

In another feature and advantage, embodiments described herein offer faster time-to-market. In particular, software developers can test new features on selected devices and deploy updates frequently, knowing that the products will remain stable. Firmware updates can be dispatched at any point in the life of the ESU; for example, while an ESU is still on a production line, with a seller, or with an end user.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

The invention claimed is:

1. A system for dynamically and remotely monitoring, maintaining, and upgrading an electrosurgical unit (ESU), the system comprising:

a remote system including computing hardware of at least one processor and memory operably coupled to the at least one processor, the remote system configured to:

receive system data over a network from the ESU, the ESU including ESU hardware of a plurality of hardware components and ESU firmware configured to operate with the plurality of hardware components, wherein the system data is received at a periodic rate and in response to an event on the ESU, and is received wirelessly at the network from the ESU;

generate a digital twin data model of the ESU, the digital twin data model being remote from the ESU;

determine if the remaining useful life of at least one of the plurality of hardware components can be extended, based on the digital twin data model;

generate a firmware update based on the determination that the remaining useful life of at least one of the plurality of hardware components can be extended, the firmware update being directed to reduce the use of the at least one of the plurality of hardware components; and transmit the firmware update over the network to the ESU, wherein the firmware update is transmitted wirelessly from the network to the ESU, and once installed, updates operation of the at least one of the plurality of hardware components.

2. The system of claim 1, wherein the digital twin model includes operational data of one or more of sensed power, current, voltage, temperature, and waveform parameters.

3. The system of claim 1, wherein the digital twin model includes hardware-specific data of one or more of processor capability, memory capability, radio circuit status, RF circuit status, power supply status, and detection circuit status.

4. The system of claim 1, wherein the remote system is further configured to generate an aggregated digital twin data model based on system data received over the network from two or more ESUs.

5. The system of claim 1, wherein the firmware update is stored on the network until the firmware update can be transmitted to the ESU.

6. The system of claim 1, wherein the firmware update is automatically installed on the ESU according to one or more predetermined update rules.

7. The system of claim 1, wherein the firmware update is not installed on the ESU until user input is received at a user interface of the remote system.

8. The system of claim 1, wherein the remote system is further configured to:

predict a fault on the ESU based on the digital twin model;

generate a firmware update based on the predicted fault; and transmit the firmware update based on the predicted fault over the network to the ESU.

9. The system of claim 8, wherein the firmware update based on the predicted fault is directed to a particular component predicted to fail.

10. A method for dynamically and remotely monitoring, maintaining, and upgrading an electrosurgical unit (ESU), the method comprising:

receiving system data over a network from the electrosurgical unit (ESU), the ESU including ESU hardware of a plurality of hardware components and ESU firmware configured to operate with the plurality of hardware components, wherein the system data is received at a periodic rate and in response to an event on the ESU, and is received wirelessly at the network from the ESU;

generating a digital twin data model of the ESU, the digital twin data model being remote from the ESU;

determining if the remaining useful life of at least one of the plurality of hardware components can be extended, based on the digital twin data model;

generating a firmware update based on the determination that the remaining useful life of at least one of the plurality of hardware components can be extended, the firmware update being directed to reduce the use of the at least one of the plurality of hardware components; and transmitting the firmware update over the network to the ESU, wherein the firmware update is transmitted wirelessly from the network to the ESU, and once installed, updates operation of the at least one of the plurality of hardware components.

11. The method of claim 10 further comprising generating an aggregated digital twin data model based on system data received over the network from two or more ESUs.

12. The method of claim 10 further comprising:

predicting a fault on the ESU based on the digital twin model;

generating a firmware update based on the predicted fault; and transmitting the firmware update based on the predicted fault over the network to the ESU.

13. The method of claim 12, wherein the firmware update based on the predicted fault is directed to a particular component predicted to fail.

14. A non-volatile computer readable storage medium comprising instructions that, when executed by a processor, cause the processor to:

receive system data over a network from an electrosurgical unit (ESU), the ESU including ESU hardware of a plurality of hardware components and ESU firmware configured to operate with the plurality of hardware components, wherein the system data is received at a periodic rate and in response to an event on the ESU, and is received wirelessly at the network from the ESU;

generate a digital twin data model of the ESU, the digital twin data model being remote from the ESU;

predict a fault on the ESU based on the digital twin data model;

determine if the remaining useful life of at least one of the plurality of hardware components can be extended, based on the digital twin data model;

generate a firmware update based on the determination that life of at least one of the plurality of hardware components can be extended, the firmware update being directed to reduce the use of the at least one of the plurality of hardware components; and transmit the firmware update over the network to the ESU, wherein the firmware update is transmitted wirelessly from the network to the ESU, and once installed, updates operation of the at least one of the plurality of hardware components.

* * * * *